United States Patent [19]
Montagnino

[11] Patent Number: 5,947,912
[45] Date of Patent: Sep. 7, 1999

[54] VIBRATORY TONGUE CONDITIONING IMPLEMENT

[75] Inventor: James Montagnino, El Paso, Tex.

[73] Assignee: Oralgiene, Culver City, Calif.

[21] Appl. No.: 08/926,676

[22] Filed: Sep. 10, 1997

[51] Int. Cl.⁶ .................................................. A61H 1/00
[52] U.S. Cl. ......................... 601/142; 606/161; 601/141; 601/46
[58] Field of Search .............................. 433/118; 601/139, 601/141, 46, 142; 606/161

[56] References Cited

U.S. PATENT DOCUMENTS

| | | |
|---|---|---|
| D. 191,189 | 8/1961 | Wisotsky . |
| D. 197,048 | 12/1963 | Troy . |
| D. 199,521 | 11/1964 | Johnson et al. . |
| D. 203,928 | 3/1966 | Terrell . |
| D. 208,626 | 9/1967 | Madl . |
| D. 267,508 | 1/1983 | Gupta . |
| D. 324,912 | 3/1992 | Hansen . |
| D. 367,707 | 3/1996 | Baker . |
| 1,738,538 | 12/1929 | Moon . |
| 1,813,630 | 7/1931 | McCarty . |
| 1,851,396 | 3/1932 | Mabry . |
| 2,011,413 | 8/1935 | Metz . |
| 2,179,402 | 11/1939 | Doran . |
| 2,218,072 | 10/1940 | Runnels . |
| 2,290,454 | 7/1942 | Steinberg . |
| 2,583,750 | 1/1952 | Runnels . |
| 2,946,072 | 7/1960 | Filler et al. . |
| 3,828,770 | 8/1974 | Kuris et al. . |
| 3,890,964 | 6/1975 | Castanedo . |
| 4,381,604 | 5/1983 | Horst . |
| 4,559,661 | 12/1985 | Tsals et al. . |
| 4,913,133 | 4/1990 | Tichy . |
| 4,995,131 | 2/1991 | Takeda . |
| 5,122,056 | 6/1992 | Barbee . |
| 5,133,661 | 7/1992 | Euvrard ................................... 433/120 |
| 5,282,814 | 2/1994 | Srivastava ............................... 606/161 |
| 5,438,726 | 8/1995 | Leite . |
| 5,573,020 | 11/1996 | Robinson ........................... 433/143 X |
| 5,613,258 | 3/1997 | Hilfinger et al. . |

*Primary Examiner*—Linda C. M. Dvorak
*Attorney, Agent, or Firm*—Watson Cole Grindle Watson, P.L.L.C.

[57] ABSTRACT

A tongue conditioning implement includes a handle, a head and a removable and replaceable cartridge including a conditioning element, the handle containing a vibrational motor to cause the implement to vibrate and reduce the manual action needed for the conditioning element to achieve the desired results. The handle can contain a switch and a battery. The head can provide a channel which extends generally transversely to the handle and the cartridge can include two end sections which enable it to snap fit onto the head. The cartridge element can be a scraper with one or more blades or a pad for the application of breath freshener gels or medications to the tongue surface.

8 Claims, 2 Drawing Sheets

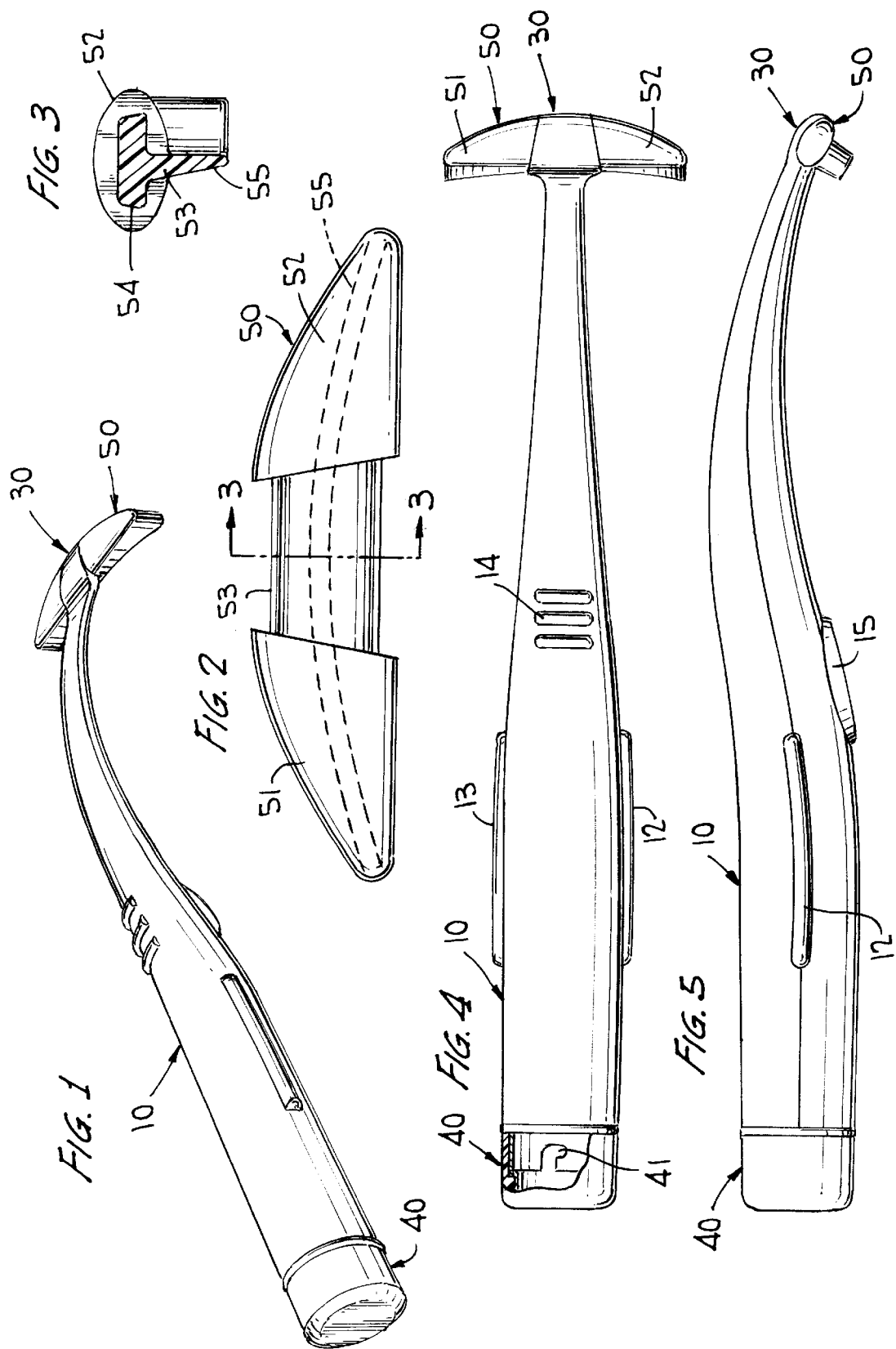

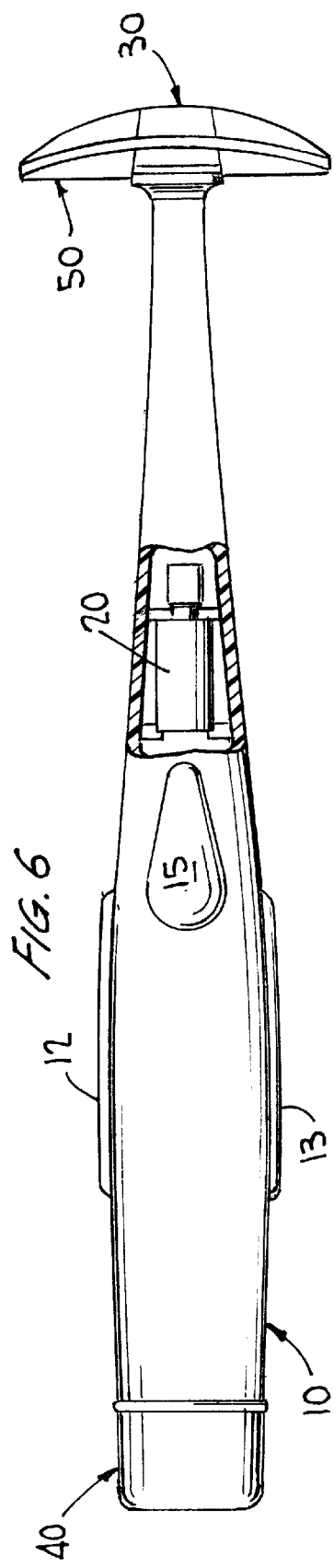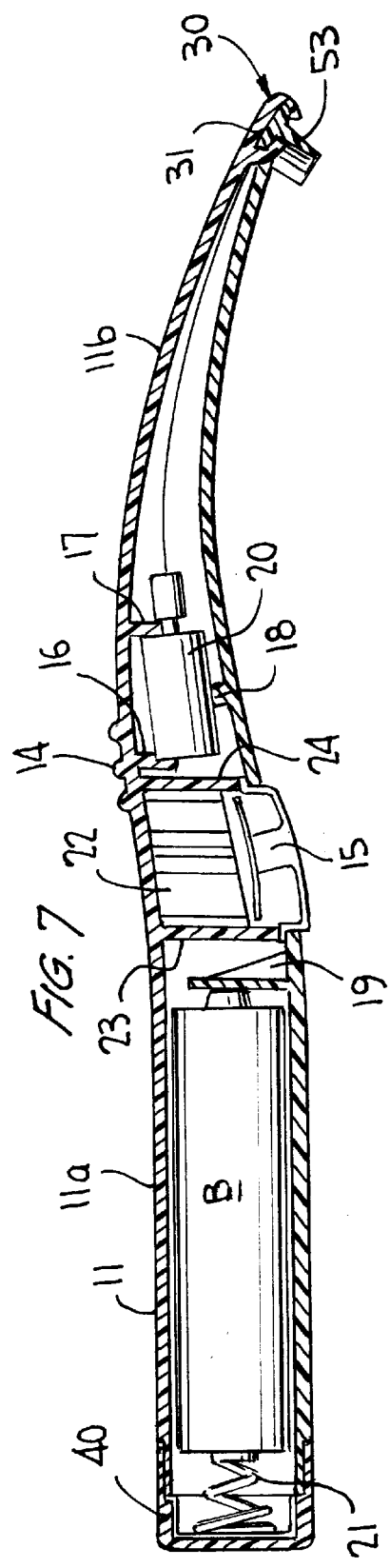

VIBRATORY TONGUE CONDITIONING IMPLEMENT

BACKGROUND OF THE INVENTION

1. Field of the Invention

The present invention relates to oral hygienic implements, and in particular to tongue conditioners.

2. The Prior Art

Implements for tongue conditioning, and more particularly tongue cleaning, although not as commonly used or advertised as toothbrushes, are nevertheless well known. See, for example, U.S. Pat. Nos. 2,218,072 and 2,583,750 to Runnels, U.S. Design Pat. No. 267,508 to Gupta, U.S. Design Pat. No. 324,912 to Hansen, and U.S. Design Pat. No. 367,707 to Baker. Although the known tongue cleaners are generally effective, they require vigorous manual action to achieve the desired results. Such vigorous manual action can cause some users to gag, which makes them less likely to continue using these implements in a manner which is effective, or indeed to use them again at all.

As such, it is an object of the present invention to provide a tongue conditioning implement which provides better conditioning action (e.g., cleaning) with less effort than the tongue conditioners known to the prior art, and which lessens any tendency of the user to gag.

SUMMARY OF THE INVENTION

According to the present invention, the object is achieved with a hand-held tongue conditioning implement which includes a handle and a head which mounts a conditioning element, and which includes a vibrational motor mounted within the handle for vibrating the handle, the head and the conditioning element, thus enhancing the effect of the conditioning element on the tongue of a user during use and reducing the amount of pressure the user needs to apply to achieve the desired results.

The inventive tongue conditioning implement also includes an electrical switch mounted within its handle which is electrically connected to the vibrational motor, an electrode post electrically connected to the switch, and an end cap with coiled spring for contacting one end of a battery positioned in the handle and for pressing the other end of the battery against the electrode post, the spring being also electrically connected to the switch. Operation of the switch by an external button causes the vibrational motor to be "on" or "off," thus controlling vibrational operation of the conditioning element, such as a scraper blade, as the user moves it along his or her tongue.

In a preferred embodiment the tongue conditioning element is in the form of a removable and replaceable cartridge which can be snap fit onto the head. In this regard, the head of the tongue conditioning implement can provide a channel which extends generally transversely to the length of the handle to accommodate the removable and replaceable cartridges, and the cartridges can include two end sections which will snap fit against the sides of the head. When used as a tongue scraper, the cartridge attached to the head will include one or more scraper blades.

Further features and advantages of the invention will be understood by reference to the attached drawings, taken with the following discussion.

BRIEF DESCRIPTION OF THE DRAWINGS

In the drawings,

FIG. 1 is a perspective view of a vibratory tongue conditioner implement constructed in accordance with a preferred embodiment of the present invention, FIG. 2 is a top plan view of the replaceable cartridge which is mounted in the head of the tongue scraper depicted in FIG. 1, FIG. 3 is a cross sectional view of the replaceable cartridge as seen along line 3—3 in FIG. 2, FIG. 4 is a top plan view of the tongue scraper depicted in FIG. 1, a portion of its base cap being broken away, FIG. 5 is a side elevational view of the tongue conditioner implement depicted in FIG. 1, FIG. 6 is a bottom plan view thereof, a portion of the handle being broken away to slow the vibrational motor mounted therein, and FIG. 7 is a cross-sectional side view thereof.

DETAILED DESCRIPTION OF THE PREFERRED EMBODIMENT

A vibrating tongue conditioner implement in accordance with a preferred embodiment of the present invention is shown in FIGS. 1–7. It includes an elongated handle portion 10, a head 30, a base cap 40 and a replaceable cartridge 50, the replaceable cartridge mounting a tongue scraper element.

As best seen in FIG. 7, the elongated handle 10 includes an outer casing 11 that defines a straight cylindrical portion 11a and a tapering, curved portion 11b. The casing can be made of metal but is preferably made of plastic. Elongated lateral ribs 12, 13 project from respective opposite sides of the casing, and a plurality of spaced parallel ribs 14 project upwardly from an upper side of the casing, these ribs enabling enhanced gripping of the casing by a user. A flexible tear-drop shaped button 15 extends downwardly from an underside of the casing to operate a switch located inside the casing, as will be discussed below.

Referring again to FIG. 7, flanges 16, 17 and 18 inside the curved handle portion 11b mount a DC vibrational motor 20 of known construction which, when operating, causes the tongue conditioning implement to vibrate. An electrode post 19 inside the cylindrical handle portion 11a is adapted to contact one end of a battery B positioned in the cylindrical handle portion, the opposite end of the battery being contacted by a coiled spring 21 that is connected to the base cap 40. The base cap 40 is removably connectable to the end of the cylindrical casing portion 11a by a bayonet connector 41. An electrical switch 22 is mounted in the casing between the electrode post and the vibrational motor 20 via cross braces 23, 24, and is electrically connected to the vibrational motor 20 on the one hand and the electrode post 19 and the coiled spring 21 on the other hand by a conductive strip which extends along the casing from the base cap to the switch (not shown). Manual operation of button 15 causes the switch 22 to alternatively electrically connect or disconnect the vibrational motor with the battery B and, via the transmission of vibration through the tapered handle portion 11b to the head 30 and the cartridge attached thereto, cause the tongue conditioning implement to be "on" (vibrating) or "off" (not vibrating).

The head 30, which is integral one piece with the end of the tapering casing portion 11b, provides a T-shaped channel 31 therein which extends generally transversely to the length of the handle 11 for a removable and replaceable cartridge 50. The cartridge 50, which is preferably made of a resilient plastic material, includes end sections 51, 52 and a curved scraper element 53 which extends between the end sections and downwardly therefrom. The scraper element, which itself has a generally T-shaped cross section, is shown to include a base 54 and a single scraper blade 55 which extends generally transversely to the base 54. The base 54 is sufficiently flexible that a portion on one side of the blade 55 (the portion between end sections 51, 52) can be extended in the channel 31 in the head 30 and the other end can snap fit into position in the channel 31, as shown in FIG. 7. Each end section 51, 52 of the cartridge will abut a side edge of the head 30. When the cartridge is to be removed, it can be twisted to dislodge the base 54 from the channel 31. The scraper element 53 can itself be rigid or flexible in construction and can be made of metal or plastic.

Although a preferred embodiment of the invention has been herein described in detail, modifications therein can be made and still fall within the scope of the appended claims. For example, instead of including only one scraper blade 55, the scraper element can include a plurality of parallel scraper blades 55 which extend downwardly from base 54. In another embodiment, instead of including a scraper blade, the removable replaceable cartridge can mount an open cell fabric pad for application of breath freshener gels or medications to a user's tongue. Also, the cartridge 50 can be removeably mounted onto the head 30 in ways other than that shown.

I claim:

1. A vibratory tongue conditioning implement which comprises:

an elongated hollow handle which contains a vibrational motor, an electrode post and an electrical switch for controlling operation of the vibrational motor, said handle defining a first end and a second end, a base cap removably attached to said first end of said handle to enable a battery to be positioned within said handle and against said electrode post, a head which is one piece with said second end of said handle, said head defining a channel which extends generally transversely to said handle, and a cartridge removable attached to said head, said cartridge extending along said channel in said head and including a conditioning element for treating a surface of a user's tongue.

2. A vibratory tongue conditioning implement according to claim 1, wherein said head defines a channel which extends generally transversely to said handle, and wherein said removable cartridge extends along said channel.

3. A vibratory tongue conditioning according to claim 1, wherein said conditioning element comprises a scraper blade.

4. A vibratory tongue conditioning implement according to claim 3, wherein said scraper blade is made of flexible material.

5. A vibratory tongue conditioning implement according to claim 1, wherein said channel is T-shaped.

6. A vibratory tongue conditioning implement according to claim 1, wherein said cartridge comprises two end sections and wherein said conditioning element extends between and downwardly from said end sections, said cartridge being extendable in and along said channel to snap fit onto said head.

7. A vibratory tongue conditioning implement according to claim 1, wherein said handle defines a cylindrical portion and a curved tapered portion, said head being one piece with an end of said curved, tapered portion remote from said cylindrical portion.

8. A vibratory tongue conditioning implement according to claim 1, including a flexible button which projects from said handle to operate said electrical switch.

\* \* \* \* \*

UNITED STATES PATENT AND TRADEMARK OFFICE
CERTIFICATE OF CORRECTION

PATENT NO. : 5,947,912
DATED : September 7, 1999
INVENTOR(S) : James MONTAGNINO

It is certified that error appears in the above-identified patent and that said Letters Patent is hereby corrected as shown below:

Title page, item

[73] Assignee: Oralgiene USA, Culver City, Calif.

Signed and Sealed this

Eleventh Day of April, 2000

Attest:

Q. TODD DICKINSON

Attesting Officer

Director of Patents and Trademarks